United States Patent [19]

Bierschenk et al.

[11] Patent Number: 4,859,747

[45] Date of Patent: * Aug. 22, 1989

[54] PERFLUORINATION OF ETHERS IN THE PRESENCE OF HYDROGEN FLUORIDE SCAVENGERS

[75] Inventors: Thomas R. Bierschenk; Timothy J. Juhlke, both of Roundrock; Richard J. Lagow, Georgetown, all of Tex.

[73] Assignee: Exfluor Research Corporation, Austin, Tex.

[*] Notice: The portion of the term of this patent subsequent to Jul. 5, 2005 has been disclaimed.

[21] Appl. No.: 198,154

[22] Filed: May 24, 1988

Related U.S. Application Data

[63] Continuation-in-part of Ser. No. 924,198, Oct. 27, 1986, Pat. No. 4,755,567, which is a continuation-in-part of Ser. No. 796,623, Nov. 8, 1985, abandoned.

[51] Int. Cl.$^4$ .................... C08G 65/32; C07C 41/22; C07C 43/12

[52] U.S. Cl. ................................. 525/409; 525/410; 568/604; 568/615; 568/639; 568/677; 568/683; 549/352; 549/353; 549/504

[58] Field of Search ............... 525/409, 410; 568/604, 568/615, 639, 677, 683; 549/352, 353, 504

[56] References Cited

U.S. PATENT DOCUMENTS

| | | | |
|---|---|---|---|
| 3,380,983 | 4/1968 | Siegart et al. | 428/375 |
| 3,429,937 | 2/1969 | Blackley et al. | 570/134 |
| 3,480,667 | 11/1969 | Siegart et al. | 549/246 |
| 3,515,582 | 6/1970 | Blackley et al. | 428/264 |
| 4,113,772 | 9/1978 | Lagow et al. | 562/583 |
| 4,330,475 | 5/1982 | Adcock et al. | 549/380 |
| 4,523,039 | 6/1985 | Lagow et al. | 568/615 |
| 4,524,032 | 6/1985 | Misaki et al. | 558/423 |
| 4,570,004 | 2/1986 | Lagow et al. | 549/352 |

OTHER PUBLICATIONS

Adcock et al., *J. Am. Chem. Soc.*, 103:6937-6947 (1981).
Maraschin and Lagow, *J. Am. Chem. Soc.*, 94:8601 (1972).
Lagow and Margrave, *Polym. Letts. Ed.*, 12:177-184 (1974).
Kowanko et al., *Fuel*, 57:769-775 (1978).
Dissertation "Aerosol Direct Fluorination: Synthesis of Perfluoroketones" by Mark Lester Robin at the University of Tennessee, Knoxville (1983).
Gerhardt and Lagow, *J. Chem. Soc. Perkin Trans* I, 1321-1328 (1981).
Gerhardt and Lagow, *J. Org. Chem.* 43:4505-4509 (1978).
Adcock et al., *J. Org. Chem.*, 40:3271-3275 (1975).

*Primary Examiner*—Earl Nielsen
*Attorney, Agent, or Firm*—Hamilton, Brook, Smith & Reynolds

[57] ABSTRACT

The direct fluorination of ethers in the presence of hydrogen fluoride (HF) scavengers such as sodium fluoride and potassium fluoride is disclosed. Ethers (liquid or solid) are either mixed with the HF scavenger, coated onto the HF scavenger or placed separately with the HF scavenger into a fluorination reactor and fluorinated by exposure to elemental fluorine. The HF scavenger permits use of more severe fluorination conditions than would be possible in the absence of the scavenger, i.e. higher initial fluorine, less gradual increases in fluorine gas concentrations and greater fluorine gas flow rates.

17 Claims, No Drawings

PERFLUORINATION OF ETHERS IN THE PRESENCE OF HYDROGEN FLUORIDE SCAVENGERS

RELATED APPLICATIONS

This application is a continuation-in-part of U.S. patent application Ser. No. 924,198, filed Oct. 27, 1986, now U.S. Pat. No. 4,755,567, issued July 5, 1988, which is a continuation-in-part of U.S. application Ser. No. 796,623, filed Nov. 8, 1985, now abandoned.

FIELD OF THE INVENTION

This invention is in the fields of polymer and fluorine chemistry.

BACKGROUND

Perfluoropolyethers have long been recognized for their outstanding thermal properties and wide liquid ranges. Perfluoropolyethers are normally made either from anionic polymerization of perfluoro epoxide or from the UV photolysis of tetrafluoroethylene or hexafluoropropylene in an inert solvent in the presence of oxygen. Both of these processes produce relatively expensive perfluoropolyethers.

The preparation of perfluoropolyethers by anionic polymerization of perfluoro epoxides first involves the oxidation of a perfluoro olefin to a perfluoro epoxide, followed by anionic polymerization of the epoxide to an acyl fluoride terminated perfluoropolyether and conversion of the acyl fluoride end groups to unreactive end groups by decarboxylation reactions or chain coupling photolytic decarboxylation reactions. The inability to form very high molecular weight polymers, the lack of stability of many perfluoro epoxides, and the extreme difficulty encountered when attempting to polymerize substituted perfluoro epoxides have been cited as drawbacks to this method. In addition, anionic polymerization of perfluoro epoxides does not lend itself well to the manufacture of perfluoro copolymers since perfluoro epoxides vary widely in reactivity.

An alternate synthetic method for the production of perfluoropolyethers involves the UV photolysis of tetrafluoroethylene and/or hexfluoropropylene in an inert solvent in the presence of oxygen. This multistep process yields an acyl fluoride terminated polymer containing —$CF_2O$—, —$CF_2$—$CF_21$— $CF_2$—$CF_2$—, —$CF_2$—$CF_2$—O—, and —$CF(CF_3)$—$CF_2$—O— repeating units as well as unstable peroxidic oxygen linkages (—$CF_2$—O—O—$CF_2$—). Treatment of the polymer at high temperatures and with fluorine gas gives a stable polymer containing perfluoroalkyl end groups. See U.S. Pat. Nos. 3,665,041; 3,847,978; 3,770,792; and 3,715,378.

Although this process can produce copolymers, the process is completely random with little control over the kinds and number of repeating units. Undesirable linkages such as the peroxidic oxygen and the poly(difluoromethylene) portions of the polymer are unavoidable. These groups can give the polymer undesirable properties for many applications. The formation of by-products and the need for fairly exotic solvents add significantly to the production costs of the polymer.

In contrast to the above-described process, direct fluorination of hydrocarbon ethers allows one to select among many more structural forms of ethers because synthetic methods for production of a wide variety of hydrocarbon ethers. The direct fluorination of hydrocarbon ethers using the LaMar process offers an economical, versatile route to production of perfluoropolyethers.

DISCLOSURE OF THE INVENTION

This invention is an improved method of directly fluorinating hydrocarbon ethers. The method comprises fluorinating the hydrocarbon ether by direct fluorination methods in the presence of a hydrogen fluoride scavenger such as sodium fluoride or potassium fluoride.

Fluorination in the presence of a hydrogen fluoride scavenger can be performed in several ways. In the preferred mode, the scavenger (in powdered or pellet form) is mixed with the ether (oil or solid form). The blend is placed in a suitable fluorination reactor and fluorinated by exposure to fluorine gas. Alternatively, the ether may be coated onto the scavenger and fluorinated in this form. Though less effective, the scavenger and the ether can be placed into the fluorination reactor separately (e.g. in separate containers).

For fluorination of polyethers, the hydrogen fluoride scavenger and the polyether should be present in a ratio of about 1:1 to 20:1 (w/w) scavenger to polyether.

The preferred method of fluorination is the LaMar procedures of direct fluorination (generally perfluorination). See Lagow, R. J. and Margrave, J. L. *Progress in Inorganic Chemistry*, 26, 161 (1979). In the LaMar process, fluorine diluted with an inert gas is passed over the ether to be fluorinated initially at low concentrations (about 0.5–10% fluorine) to minimize fragmentation of the ether. As the fluorination reaction proceeds, the fluorine concentration and flow rate of the gas are gradually increased until pure fluorine conditions are achieved and the ether is perfluorinated. Alternatively an initial fluorine concentration for the desired fluorination can be selected and maintained throughout fluorination reaction.

The presence of a hydrogen fluoride scavenger allows the use of more severe fluorination conditions in this direct fluorination procedure, that is, higher fluorine concentrations and faster rates of fluorine delivery can be used in the presence of a hydrogen fluoride scavenger than can be used in the absence of a scavenger. For example, in the fluorination of polyethylene oxide initial fluorine levels of over 15% and up to 25% and fluorine flow rates of over 8 cc/min/gram of polymer can be used. In the absence of the scavenger, severe charring of the ether can occur under these conditions.

In addition, the yield and quality of the perfluoropolyether product is improved when fluorination is conducted in the presence of a hydrogen fluoride scavenger. The scavenger is believed to prevent the formation of ether-HF acid base complexes during the fluorination reaction. Sodium fluoride will react with hydrogen fluoride produced during fluorination to give sodium bifluoride (NaF+HF NaHF$_2$) thus eliminating HF and preventing reaction of the HF with oxygen linkages of the ether.

The method of this invention can be used to fluorinate polyethers e.g. linear polyethers such as polyethylene oxide, polypropylene oxide, and copolymers of ethylene oxide/methylene oxide of ethylene oxide/propylene oxide as well as simple ethers such as THF.

BEST MODE OF CARRYING OUT THE INVENTION

Sodium fluoride (NaF) is the preferred hydrogen fluoride scavenger for the fluorination procedure of this invention but others such as potassium fluoride can be used. The NaF can be in the form of pellets or powder, and the hydrocarbon ether may be in a solid or a liquid form.

In the preferred mode of this invention, the hydrogen fluoride scavenger is mixed with the hydrocarbon ether to be fluorinated, and the mixture is fluorinated in a fluorination apparatus by direct fluorination procedures to the desired level of fluorination.

In an alternate mode, the ether can be coated onto the hydrogen fluoride scavenger and fluorinated in this form. Solvents may be used to dissolve the ether and then coat it on. For example, NaF powder or pellets can be used in the fluorination of liquid ethers; the use of NaF powder may be preferred because the powder has more surface area than the pellets. Consequently, coating the ether onto the powder increases the surface area of the liquid which is available for reaction with fluorine gas. A liquid ether can be coated on the powder neat without use of a solvent.

If the ether is a solid, pellets of the hydrogen fluoride scavenger are preferred because the solid perfluoroether product can be easily separated from the pellets using a coarse screen. However, solids that do not powder well may be best handled by coating them on NaF powder to increase the surface area. Such solids can be dissolved, mixed with the NaF, and then dried to coat them on the NaF. Alternately, they may be coated neat if done above the melting point or in a mixer that will break up the solid ether.

Generally, the form of sodium fluoride or other scavenger to be used and treatment, if any, needed to coat the ether on the sodium fluoride may be ascertained by routine experiment with the particular ether.

The fluorination of the ether in the presence of hydrogen fluoride scavengers can be performed in a variety of reactors. Stationary metal tubes, rotating drum reactors, fluidized beds, and solvent reactors are all conducive to the method. In a solvent reactor, the ether can be soluble in the solvent or the reaction may take place on a slurry or emulsion. In stationary tube reactors, the ether and the sodium fluoride powder or pellets should be mixed together fairly evenly. Placing the sodium fluoride in one end of the reactor and the ether in the other end is not as effective as mixing the two together.

The amount of sodium fluoride added is ideally the stoichiometric amount needed to react with all of the hydrogen fluoride formed in the reaction. Because sodium fluoride will react with more than one equivalent of hydrogen fluoride at temperatures below 100° C., somewhat less than a stoichiometric quantity can be used. Also, the perfluoro and partially fluorinated ethers do not complex hydrogen fluoride as strongly as hydrocarbon ethers so less than a stoichiometric quantity may be used although best results are obtained with at least half of the stoichiometric amount of sodium fluoride. When using pellets, it may be best to use somewhat more THAN the stoichiometric quantity of HF as the crushing strength of the pellets is reduced if they absorb more than a stoichiometric quantity of HF.

In the perfluorination of polyethylene oxide, for example, some benefit is derived in the yield and quality of the perfluoroethers produced if as little as a 1:1 ratio is used. Optimal results are obtained for this polymer with a 4:1 by weight mixture of sodium fluoride to polyethylene oxide. This is about the stoichiometric ratio. The use of more than a 4:1 by weight ratio does not improve the process. However, if pellets of NaF are used, a ratio of greater than 4:1 may be desirable because this prevents the pellets from absorbing more than a stoichiometric quantity of hydrogen fluoride. For liquid polyethers such as low molecular weight polyethylene glycol, much more than a stoichiometric quantity may be desired so the fluorination can be done on a free flowing powder rather than a paste.

Once the ether and sodium fluoride are placed in the reactor, fluorine gas which may be diluted with helium, nitrogen or other inert gas is introduced in the reactor. With a hydrogen fluoride scavenger present initial fluorine concentration can range from 0.5% fluorine up to as high as 25% fluorine. In general, the highest dilution of fluorine and the lowest flow rate of fluorine are used at the beginning of the reaction as the ether is generally most reactive and most susceptible to burning or fragmentation at this stage.

Oxygen can also be introduced into the system, if desired, to increase the amount of terminal acid groups on the perfluoroethers produced.

As the fluorination proceeds, the fluorine concentration is raised and the fluorine flow rate may also be increased. If desired, the temperature can be raised before the reaction is complete to induce fragmentation or the ether may be heated to about 100° C. in the presence of fluorine at the end of the reaction to eliminate terminal acid groups.

In practice, it is often more convenient to set the fluorine and inert gas flow at the beginning of the reaction and maintain the initial flow throughout the reaction. This can be done satisfactorily when an HF scavenger such as NaF is used. For example, yields of about 80% can be achieved in the fluorination of polyethylene oxide when 25% fluorine is used from start to finish.

When the reaction is complete, the reactor is purged of excess fluorine and the products are removed. The product can be extracted with water to remove the sodium bifluoride/sodium fluoride or solvents can be used to extract the fluorinated ethers. If pellets of sodium fluoride are used, the products can be separated using a coarse sieve.

The fluorination reaction can be done on a batch basis with times varying from a few hours to several days. Reactions can be performed in as little as six hours and as long as two weeks. The preferred time scale depends upon the reactor system and there are virtually no limits to the theoretically shortest time as long as the heat transfer is sufficient to prevent unacceptable amounts of polymer fragmentation.

Fluorination reactions can be done at temperatures ranging from about $-120°$ C. to about 200° C. Above about 350° C. addition of NaF will not complex hydrogen fluoride. At very low temperatures, NaF would probably do very little good as the hydrogen fluoride would not have enough volatility to move out of the ether into the sodium fluoride. The preferred temperature range is from $-40°$ C. to 140° C.

Perfluoropolyethers, due to their good stability and chemical inertness, are useful for many applications. For example, perfluoropolyether oils, such as perfluoropolymethylene oxide and perfluoropolyethylene oxide are useful as high performance lubricants. Current synthetic methods for perfluoroethers are expensive and consequently have enjoyed limited use. Because the direct fluorination process requires relatively inexpensive starting materials (hydrocarbon ethers and fluorine), it is an economical method of producing perfluoropolyethers. The presence of a hydrogen fluoride scavenger during the fluorination of hydrocarbon ethers allows the use of very simple reactors to achieve results comparable to those achieved without a hydrogen fluoride scavenger (i.e. when extremely dilute fluorine is used and very long reaction times are used to minimize ether-HF complex formation). Hydrogen fluoride scavengers added to the hydrocarbon polyether allow the use of relatively harsh fluorination conditions yet provide good quality perfluoropolyethers and good yields. The method of this invention improves the economy and efficiency of direct fluorination of hydrocarbon polyethers and allows the manufacture of inexpensive perfluoropolyethers. A wide range of ether structures are available by this process because it is possible to produce a wide range of hydrocarbon polyethers by well-established synthetic techniques.

The advantages gained by the addition of NaF to polyethers for fluorination are illustrated by the example given below. Three samples were placed in identical reactors and treated with the same fluorination conditions. The first sample contained only 1M MW polyethylene oxide, the second contained a 9:1 mixture of sodium bifluoride (NaHF$_2$) and 1M MW polyethylene oxide and the third contained a 4:1 mixture of NaF and 1M MW polyethylene oxide. The second sample contained a lot of sodium bifluoride to show that the sodium fluoride does not simply act as an inert powder which prevents the small polyethylene oxide particles from sticking together and reducing the surface area available for reaction. The results obtained with each sample are summarized in the table below.

rination conditions are used. Initial fluorine levels of over 15% and fluorine addition rates of over 8 cc/min per gram of polyethylene oxide starting material have been used to shorten the reaction time to about six hours. If the same reaction is tried without sodium fluoride, severe charring occurs. With sodium fluoride, such severe reaction conditions still give about an eighty percent yield of perfluoropolyethylene oxide with a more linear structure than perfluoropolyethylene oxide prepared with much milder conditions when sodium fluoride is not used.

The advantages of using a hydrogen scavenger are also pronounced when pure fluorine is used throughout the reaction As expected, the fluorination of polyethylene glycol with pure fluorine almost always results in complete combustion or charring. However, if the polyethylene glycol is mixed with NaF powder, the entire reaction can be carried out using pure fluorine and yields in excess of 40% are typically obtained. Fluorination with pure fluorine offers several advantages over fluorination with dilute fluorine. Most notably, if the material to be fluorinated has an appreciable vapor pressure at the fluorination temperature, it is often desirable to use pure fluorine to prevent the reactant from being swept out of the reactor before it becomes perfluorinated.

The invention is further illustrated by the following examples.

EXAMPLE 1

480 grams of high molecular weight (1 million) polyethylene oxide was mixed with 2400 grams sodium fluoride pellets and placed in a rotating drum reactor with a volume of about twenty liters. After purging for two hours at 3 liters per minute nitrogen flow, the fluorine flow is set at 480 cc/min and the nitrogen flow is set at 3 liters per minute. These conditions are maintained

| Sample #1 | Sample #2 | Sample #3 |
| --- | --- | --- |
| 2 grams 1 $\overline{M}$ MW Polyethylene oxide ground to pass 100 mesh. | 2 grams 1 $\overline{M}$ MW Polyethylene oxide ground to pass 100 mesh mixed with 18 g NAHF$_2$ powder ground to pass 100 mesh. | 2 grams 1 $\overline{M}$ MW Polyethylene oxide ground to pass 100 mesh mixed with 8 g NaF ground to pass 100 mesh. |
| Dried in 100 cc/min N$_2$ flow several hours. | Dried in 100 cc/min N$_2$ flow several hours. | Dried in 100 cc/min N$_2$ flow several hours. |
| Fluorination Program: | Fluorination Program: | Fluorination Program: |
| 2 cc/min F$_2$, 100 cc/min N$_2$ for 47 hours. | 2 cc/min F$_2$, 100 cc/min N$_2$ for 47 hours. | 2 cc/min F$_2$, 100 cc/min N$_2$ for 47 hours. |
| 2 cc/min F$_2$, 25 cc/min N$_2$ for 4 hours. | 2 cc/min F$_2$, 25 cc/min N$_2$ for 4 hours. | 2 cc/min F$_2$, 25 cc/min N$_2$ for 4 hours. |
| 2 cc/min F$_2$, 0 cc/min N$_2$ for 13 hours. | 2 cc/min F$_2$, 0 cc/min N$_2$ for 13 hours. | 2 cc/min F$_2$, 0 cc/min N$_2$ for 13 hours. |
| Results: 0.7 g weight gain, sticky solid. Solids extracted with Freon 113 to give 0.82 g oil, 1.9 g insoluble solids. | Results: 1.1 g weight gain, free-flowing powder. Solids extracted with Freon 113 to give 0.46 g oil. Solids then extracted with water to give 2.4 g solids. | Results: 6.0 g weight gain, free-flowing powder. Solids extracted with Freon 113 to give 0.50 g oil. Solids then extracted with water to give 4.4 g solids. |
| Overall Yield: 2.7 g (51%) | Overall Yield: 2.86 g (54%) | Overall Yield: 4.9 g (93%) |

In addition to the yield improvement, analysis of the oil in the $^{19}$F NMR reveals a more linear structure when sodium fluoride is used as there are many fewer CF groups in the NMR. This results in an oil that has a lower pour point with the same viscosity oil at room temperature.

The advantage gained by the addition of sodium fluoride is even more dramatic when more severe fluofor about 36 hours at which time the nitrogen flow is reduced to 1.5 liters per minute and the fluorine flow is maintained at 480 cc/min. These conditions are maintained for about 8 hours and then the nitrogen flow is cut off and the reactor is exposed to pure fluorine at 480 cc/min for 4 hours or until a significant amount of fluorine comes out of the reactor. The perfluoropolyethylene oxide is then separated from the NaF/NaHF$_2$ by sieving through a coarse screen. About 1030 grams of perfluoro- polyethylene oxide solids are obtained (81.4% yield).

EXAMPLE 2

480 g of high molecular weight (1 million) polyethylene oxide was mixed with 2,400 g sodium powder (passed 100 mesh sieve) and placed in a rotating drum reactor. After purging for two hours at 3 liters per minute nitrogen flow, the fluorine flow was set at 480 liters per minute. These conditions were maintained for about 36 hours at which time the nitrogen flow was reduced to 1.5 liters per minute and the fluorine flow was maintained at 480 cc/min. These conditions were maintained for about 8 hours and then the nitrogen flow was cut off and the reactor contents were exposed to pure fluorine (480 cc/min) for 4 additional hours (or until a significant amount of fluorine comes out of the reactor). The perfluoropolyethylene oxide was separated from the NaF/NaHF$_2$ by washing with approximately 15 gallons of water. About 1050 g of perfluoropolyethylene oxide solids were obtained (83%).

EXAMPLE 3

80 g of 1M molecular weight polyethylene oxide was mixed with 400 g sodium fluoride pellets and placed in a rotating drum reactor. After purging the reactor for 2 hours with 3 liters per minute nitrogen flow, the fluorine flow was set at 640 cc/min and the nitrogen flow was set at 4 liters per minute. These conditions were maintained for bout 4 hours at which time the nitrogen flow was reduced to 2 liters per minute and the fluorine flow was maintained at 640 cc/min. These conditions are maintained for an additional 2 hours at which time the nitrogen flow was cut off and the reactor contents was exposed to pure fluorine (640 cc/min) for one additional hour (or until a significant amount of fluorine comes out of the reactor). The NaF/NaHF$_2$ was separated from the product using a screen to give 158 g of perfluoropolyethylene oxide (74.9% yield).

EXAMPLE 4

78.6 g of 4M molecular weight polyethylene oxide was dissolved in methylene chloride and mixed with 314.4 g of NaF powder (passes a 100 mesh screen). The methylene chloride was evaporated leaving behind a solid which was ground to give a 50 mesh powder. The powder was loaded in a rotating drum reactor which was purged for 2 hours with 3 liters per minute nitrogen prior to beginning the reaction. Fluorine gas (80 cc/min) diluted with nitrogen (4 liters per minute) was passed over the powder for approximately 36 hours (reactor temperature 30°-40° C.). Next, the nitrogen flow was reduced to 1.5 liters per minute while the fluorine flow was maintained at 80 cc/min. These conditions were maintained for 8 hours and then the product was exposed to 80 cc/min pure fluorine for several hours to ensure perfluorination. The NaF/NaHF$_2$ was dissolved in water leaving behind 174 g of a perfluoropolyethylene oxide solid (84.0% yield).

EXAMPLE 5

320 g of 600 MW polyethylene glycol was mixed with 1280 g sodium fluoride powder. The mixture was placed in a rotating drum reactor and fluorinated at 30°-40° C. using 320 cc/min fluorine and 16 liters per minute nitrogen (36 hours). The nitrogen was decreased to 1.5 liters/minute and the fluorination was allowed to continue for an additional 12 hours. The polymer was treated with pure fluorine for several hours to ensure perfluorination. A final fluorination at 110° C. for 4 hours was used to convert reactive acetyl fluoride end groups to inert trifluoromethyl or pentafluoroethyl end groups. Extraction of the product with liters Freon 113 gave 752 g of perfluoropolyethylene oxide oil. An additional 32 g of Freoninsoluble perfluoropolyether solids were recovered by dissolving the NaF/NaHF$_2$ coproduct in water (total yield of 92.9%).

EXAMPLE 6

200 g of polypropylene oxide (thick oil) was dissolved in 750 milliliters of methylene chloride and was mixed with 1500 g of sodium fluoride powder. After removal of the solvent the mixture was sieved through a 50 mesh sieve to give a more uniform particle size. Fluorination of the mixture using 200 cc/min fluorine with decreasing amounts of nitrogen (similar to the programs used in the previous examples) gave 160.4 g of a Freon soluble oil ($^{19}$F nmr was identical to that obtained for a Krytox TM fluid (also a perfluoropolypropylene oxide) along with 240 g of perfluoropolypropylene oxide solids (total yield of 69.9%).

EXAMPLE 7

A similar fluorination of a 70:30 ethylene oxide:propylene oxide copolymer (wax) was carried out. 480 g of copolymer was dissolved in 2 liters of methylene chloride and was coated on 2400 g of sodium fluoride powder. A gas flow of 300 cc/min fluorine and 3 liters per minute nitrogen was maintained for 36 hours. The nitrogen was decreased to 1 L/min for an additional 12 hours. The polymer was treated with pure fluorine for several hours prior to treatment with pure fluorine at 110° C. to remove the reactive end groups (6 hours). Extraction of the product with Freon 113 gave 495 g oil. Removal of the NaF/NaHF$_2$ gave an additional 356 g of perfluoropolyether solids (total yield 64.1%).

EXAMPLE 8

300 g of polydioxolane powder was dissolved in 500 ml of methylene chloride and mixed with 1200 g NaF powder. The solvent was evaporated and the resulting solid was ground cryogenically to give a powder which will pass a 50 mesh screen. The powder was placed in a 9" ID×2' long aluminum drum reactor which rotates at 5 rev./min. The reactor was flushed with nitrogen for several hours prior to beginning the fluorination. A gas flow of 300 cc/min fluorine and 2 L/min nitrogen was maintained for 36 hours. The nitrogen was decreased to 1 L/min for an additional 12 hours. The polymer was treated with pure fluorine for several hours to insure perfluorination. A reactor temperature between 0° C. and +20° C. was desirable for best results. A final fluorination at 110° C. for 4 hours was used to replace any residual hydrogen with fluorine and to convert reactive acetyl fluoride end groups to inert trifluoromethyl or pentafluoroethyl terminal groups. Extraction of the powder with 2 liters of Freon 113 gave 370 g of the desired difluoromethylene oxide-tetrafluoroethylene oxide copolymer. An additional 160 g of a Freon insoluble solid was also obtained which can be converted to a fluid via pyrolysis. Elemental analysis for solid: calculated (C$_3$F$_6$O$_2$)$_n$: C, 19.80; F, 62.63, found: C, 18.11; F, 62.53.

EXAMPLE 9

Two grams of polydioxolane were placed in a nickel boat along with 10 g of NaF pellets (⅛" mesh). The boat was placed in a 1½" nickel tube reactor and flushed with 100 cc/min N$_2$ prior to beginning the fluorination. The fluorine and nitrogen flow rates were set at 2 cc/min and 100 cc/min, respectively. After 48 hours had elapsed, the sample was treated for 12 hours with pure fluorine at 100° C. Extraction of the product mixture with Freon 113 gave 1.5 g of a clear, low viscosity, nonvolatile oil. The NaF/NaHF$_2$ pellets were screened from the sample leaving behind 0.4 g of a white solid (Total yield: 38.6%). Infrared analysis and the NMR spectra of the oil were very similar to that observed for the oil prepared according to Example 1.

EXAMPLE 10

Fluorination of polydioxolane using the very mild conditions as described in Examples 1 and 2 gives a perfluoro product with a minimal amount of chain degradation occurring during the fluorination reaction. The oil present in the sample results from the direct fluorination of lower molecular weight chains in the hydrocarbon starting material. The oil to solid ratio of the final product can be increased by employing a two-step direct fluorination process. In the initial phase, dilute fluorine is passed over the sample to replace the majority of the hydrogen. The second step, perfluorination of the sample with pure fluorine at elevated temperature, give a product with a lower average molecular weight. The exothermicity of the reaction with elemental fluorine results in some chain fragmentation.

Two grams of polydioxolane was mixed with 10 g of NaF powder. The reactor was purged with 100 cc/min N$_2$ for 1 hours, followed by reaction of the polymer with 2 cc/min F$_2$ diluted with 100 cc/min N$_2$ for 48 hours. Next, the polymer was subjected to pure fluorine at 100° C. for 8 hours at which time some chain cleavage occurred. Using this procedure, 2.4 g of oil and 0.1 g of solid material are obtained (50.8% total yield).

EXAMPLE 11

A brass pipe reactor (3 in. I.D.×2 ft. long) was loaded with 600 g sodium fluoride powder and 122 g polyethylene glycol having an average molecular weight of 400 (acetyl end groups). The reactor was purged with nitrogen (100 cc/min) for 30 minutes prior to starting the reaction. Pure fluorine was introduced into the reactor at a rate of 65 cc/min for approximately 75 hours while the reactor was maintained near room temperature. The fluorine flow was then reduced to 10 cc/min. and the reactor was warmed over a 1.5 hour period to 100° C. The fluorine flow was terminated and the reactor was purged with nitrogen (50 cc/min) while the reactor temperature was further raised to 200° C. A liquid product (111 g, 43% yield) was collected in a 0° C. trap which was placed at the end of the reactor. A solid residue (860 g) remained in the reactor which, when washed with several gallons of water, yielded 138 g of a water-insoluble fluorocarbon solid.

EXAMPLE 12

Polypropylene glycol (86 g) having an average molecular weight of 425 was mixed with sodium fluoride powder (600 g) and placed in a brass tube reactor (3 in. I.D.×2 ft. long). After the reactor was purged with nitrogen (200 cc/min), fluorine was introduced at a rate of 66 cc/min while the nitrogen flow was terminated. The fluorine flow was maintained for approximately 67 hours, then reduced to 10 cc/min. The reactor was warmed over a 30 minute period to 130° C. The fluorine was then shut off, the nitrogen flow was set at 100 cc/min and the reactor was allowed to warm to 270° C. A liquid product (72.5 g, 38% yield) was collected in a 0° C. trap downstream from the reactor. After washing the nonvolatile solids left in the reactor with water, 115 g of a solid fluorocarbon product was obtained.

EXAMPLE 13

320 of 200 mw polyethylene glycol was dissolved in 500 ml methylene chloride was mixed with 1280 g sodium fluoride powder. The mixture was placed in a rotating drum reactor and fluorinated at 30° C. using 320 cc/min fluorine and 2.5 liters/min nitrogen for 52 hours. Extraction of the product with 3 liters Freon 113 gave 760 g of a highly fluorinated poly(ethylene oxide) oil. Post-treatment of the oil at 250° C. gave 750 g perfluoropoly(ethylene oxide) fluid.

INDUSTRIAL APPLICABILITY

Because the direct fluorination process requires relatively inexpensive starting materials i.e. hydrocarbon polyethers and fluorine, this is a viable method of producing perfluoropolyethers. The addition of sodium fluoride to the hydrocarbon polyethers in the fluorination allows one to use very simple reactors to commercially produce perfluoropolyethers of good quality. It may be possible to get as good results without a hydrogen fluoride scavenger if extremely dilute fluorine is used and very long reaction times are used to keep the ether-HF complex from forming in the reactor to any great extent. However, hydrogen fluoride scavengers such as sodium fluoride or potassium fluoride added to the hydrocarbon polyether allow one to use relatively harsh fluorination conditions and still achieve good quality perfluoropolyethers and good product yield. The improvement of this invention provides for economic, large scale fluorination of hydrocarbon polyethers and makes the manufacture of inexpensive perfluoropolyethers possible. Polyethers of a wide range of structures can be fluorinated by this process because it is possible to produce a great variety of hydrocarbon polyethers.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of fluorinating a hydrocarbon ether, comprising contacting the hydrocarbon ether, in the presence of a hydrogen fluoride scavenger, with fluorine gas under conditions sufficient for fluorination of ether, the amount of hydrogen fluoride scavenger being sufficient to react with hydrogen fluoride formed during the fluorination and to prevent charring or combustion of the ether during the fluorination.

2. A method of claim 1, wherein the hydrocarbon ether is a polyether.

3. A method of claim 2, wherein the polyether is a linear polyether.

4. A method of claim 1, wherein the hydrogen fluoride scavenger is sodium fluoride.

5. A method of claim 1, wherein pure fluorine gas is used for the fluorination.

6. A method of claim 1, wherein the ether is coated onto the hydrogen fluoride scavenger.

7. A method of claim 1, wherein the hydrogen fluoride scavenger and the ether are present in a weight ratio of about 1:1 to about 20:1.

8. A method of claim 1, wherein the hydrogen fluoride scavenger is in powder or pellet form.

9. A method of claim 1, wherein the reactor is a stationary metal tube, a rotating drum reactor, a fluidized bed reactor or a solvent reactor.

10. A method of perfluorinating a polyether, comprising:
   a. placing the polyether and hydrogen fluoride scavenger in a fluorine reactor, the amount of hydrogen fluoride scavenger being sufficient to react with hydrogen fluoride formed during fluorination; and
   b. fluorinating the polyether by introducing fluorine into the reactor under conditions sufficient for perfluorination.

11. A method of claim 10, wherein the polyether is a linear polyether.

12. A method of claim 10, wherein the hydrogen fluoride scavenger is sodium fluoride.

13. A method of claim 10, wherein the polyether and the hydrogen fluoride scavenger are mixed together.

14. A method of claim 10, wherein the ether is coated onto the hydrogen fluoride scavenger.

15. A method of claim 10, wherein the hydrogen fluoride scavenger and the ether are present in a weight ratio of about 1:1 to about 20:1.

16. A method of claim 10, wherein the hydrogen fluoride scavenger is in powder or pellet form.

17. A method of claim 10, wherein the reactor is a stationary metal tube, a rotating drum reactor, a fluidized bed reactor or a solvent reactor.

* * * * *